(12) United States Patent
Saito et al.

(10) Patent No.: US 9,477,808 B2
(45) Date of Patent: Oct. 25, 2016

(54) MEDICAL INFORMATION MANAGEMENT APPARATUS, MEDICAL INFORMATION MANAGEMENT METHOD, AND MEDICAL SYSTEM

(71) Applicant: Toshiba Medical Systems Corporation, Otawara-shi (JP)

(72) Inventors: Hiroki Saito, Otawara (JP); Yosuke Hirasawa, Sakura (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 108 days.

(21) Appl. No.: 14/335,081

(22) Filed: Jul. 18, 2014

(65) Prior Publication Data
US 2015/0023474 A1    Jan. 22, 2015

(30) Foreign Application Priority Data
Jul. 19, 2013   (JP) .................................. 2013-150689

(51) Int. Cl.
H05G 1/28       (2006.01)
G06F 19/00      (2011.01)
A61B 6/00       (2006.01)

(52) U.S. Cl.
CPC ......... *G06F 19/321* (2013.01); *G06F 19/3481* (2013.01); *A61B 6/542* (2013.01)

(58) Field of Classification Search
CPC .......... H05G 1/26; H05G 1/265; H05G 1/28; H05G 1/30; H05G 1/32; H05G 1/38; H05G 1/46; A61B 6/54; A61B 6/542; A61B 6/545; G03B 42/02
USPC ............ 378/96, 97, 98, 98.5, 98.7, 108, 165
See application file for complete search history.

(56) References Cited

U.S. PATENT DOCUMENTS 6,795,526 B2 * 9/2004 Kump .................... A61B 6/544
                                                       378/116

FOREIGN PATENT DOCUMENTS

JP         2007-097909         4/2007

\* cited by examiner

*Primary Examiner* — Jurie Yun
(74) *Attorney, Agent, or Firm* — Oblon, McClelland, Maier & Neustadt, L.L.P.

(57) ABSTRACT

According to one embodiment, a medical information management apparatus includes an examination information acquisition unit acquiring examination information including an irradiation condition, an imaging region and an exposure dose for each examination on the imaging region, an archiving unit archiving an exposure dose calculation target region classified more detailed than the imaging region and a weight coefficient corresponding to the exposure dose calculation target region in association with the irradiation condition and the imaging region, a weight coefficient acquisition unit acquiring a weight coefficient corresponding to the exposure dose calculation target region based on the irradiation condition acquired by the examination information acquisition unit and the exposure dose calculation target region archived in the archiving unit, and a calculation unit calculating an exposure dose at the exposure dose calculation target region by using an exposure dose for each examination and the weight coefficient.

21 Claims, 6 Drawing Sheets

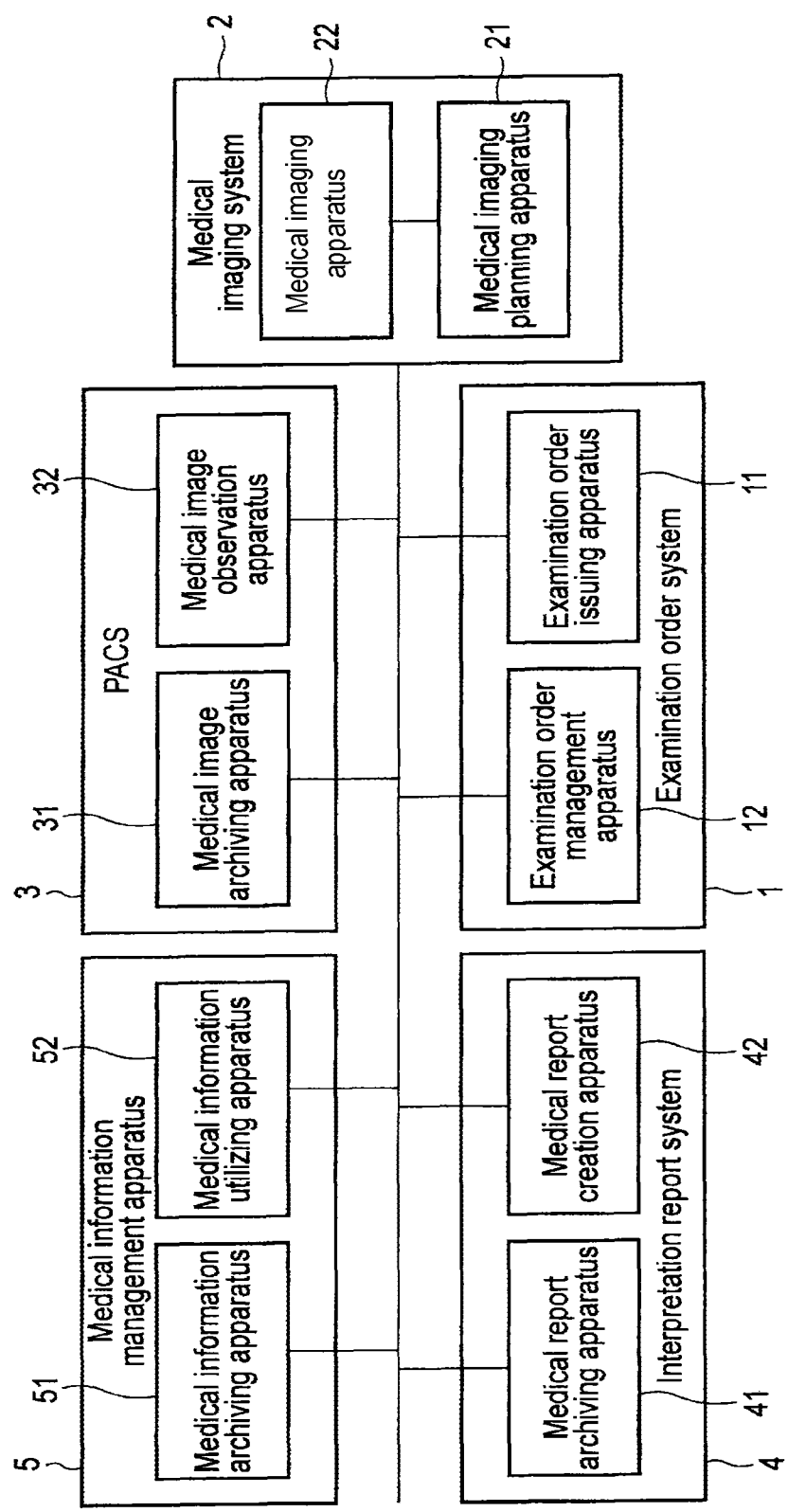
F I G. 1

| | Device type | Imaging region | Sex | Image laterality | Irradiation direction | Irradiation region | Weight coefficient |
|---|---|---|---|---|---|---|---|
| Lookup sample a | General imaging | Chest region | Male | N/A | Front | Lung | 0.20 |
| | General imaging | Chest region | Male | N/A | Front | Heart | 0.21 |
| | General imaging | Chest region | Male | N/A | Front | Thyroid gland | 0.10 |
| | ... | ... | ... | ... | ... | ... | ... |
| Lookup sample b | General imaging | Chest region | Female | N/A | Front | Lung | 0.20 |
| | General imaging | Chest region | Female | N/A | Front | Heart | 0.21 |
| | General imaging | Chest region | Female | N/A | Front | Left breast | 0.25 |
| | ... | ... | ... | ... | ... | ... | ... |
| Lookup sample c | General imaging | Chest region | Male | N/A | Back | Lung | 0.30 |
| | General imaging | Chest region | Male | N/A | Back | Heart | 0.17 |
| | General imaging | Chest region | Male | N/A | Back | Thyroid gland | 0.05 |
| | ... | ... | ... | ... | ... | ... | ... |
| Lookup sample d | Mammography | Chest region | Female | L | N/A | Left mammary gland | 0.80 |
| | Mammography | Chest region | Female | L | N/A | Left breast (fat) | 0.20 |
| Lookup sample e | Mammography | Chest region | Female | R | N/A | Right mammary gland | 0.80 |
| | ... | ... | ... | ... | ... | ... | ... |
| Lookup sample f | CT | Head region | Male | N/A | N/A | Brain | 0.30 |
| | CT | Head region | Male | N/A | N/A | Eye ball | 0.20 |
| | ... | ... | ... | ... | ... | ... | ... |

Examination information

F I G. 3

Exposure information

| Patient identification | Examination identification | Irradiation region | Irradiation region exposure dose |
|---|---|---|---|
| A | 1 | Lung | 20 |
| A | 1 | Heart | 21 |
| A | 1 | Thyroid gland | 10 |
| A | 1 | ... | ... |
| A | 2 | Lung | 30 |
| A | 2 | Heart | 17 |
| A | 2 | Thyroid gland | 5 |
| A | 2 | ... | ... |
| A | 3 | Brain | 30 |
| A | 3 | Eye ball | 20 |
| A | 3 | ... | ... |

FIG. 4

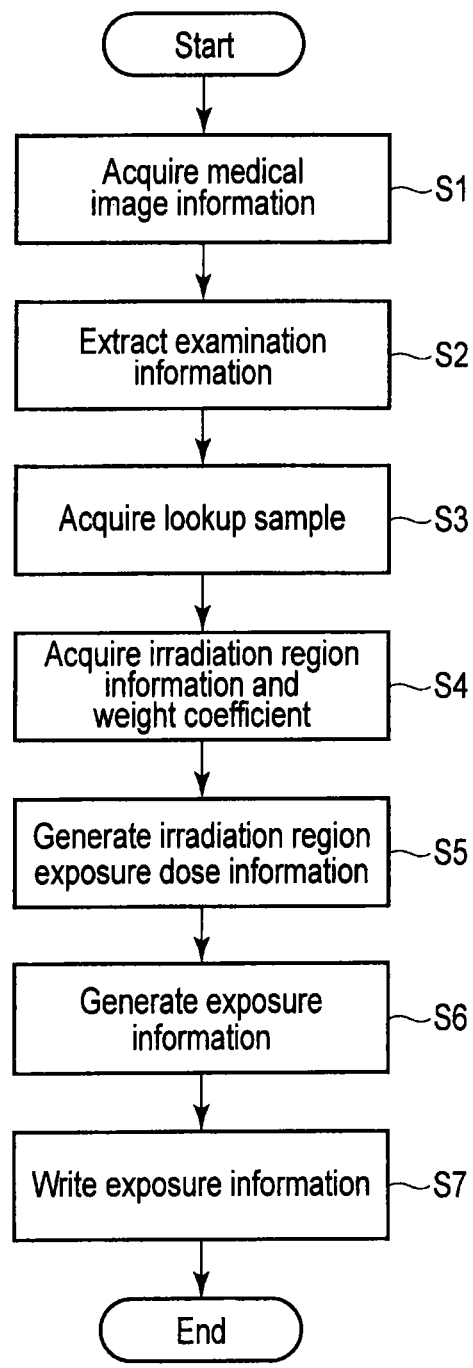
F I G. 6

US 9,477,808 B2

MEDICAL INFORMATION MANAGEMENT APPARATUS, MEDICAL INFORMATION MANAGEMENT METHOD, AND MEDICAL SYSTEM

CROSS-REFERENCE TO RELATED APPLICATION

This application is based upon and claims the benefit of priority from the prior Japanese Patent Application No. 2013-150689, filed Jul. 19, 2013 the entire contents of which are incorporated herein by reference.

FIELD

Embodiments described herein relate generally to a medical information management apparatus, a medical information management method, and a medical system.

BACKGROUND

Recently, an environmental improvement has been made for the management of the doses of medical radiation (to be referred to as the radiation doses hereinafter). For example, J-RIME (Japan Network for Research and Information on Medical Exposures) has been established and Dose SR (Dose Structure Report) has been defined by IHE (Integrating the Healthcare Enterprise).

In addition, there have been developed management techniques of managing the dose of exposure (to be simply referred to as the exposure dose hereinafter) for each examination performed by using various types of medical imaging apparatuses (for example, an X-ray diagnostic apparatus and an X-ray CT (Computed Tomography)) using radiation and an accumulated exposure dose for a predetermined period. However, these techniques do not have any function of managing an exposure dose for each region such as the lung, heart, or thyroid gland.

It is an objective to provide a medical information management apparatus, medical information management method, and medical system which can manage an exposure dose for each of such regions.

BRIEF DESCRIPTION OF THE DRAWINGS

FIG. 1 is a schematic view showing an example of the schematic arrangement of a medical system including a medical information management apparatus according to an embodiment;

FIG. 3 is a schematic view showing an example of a lookup table according to the embodiment;

FIG. 4 is a schematic view showing an example of the data structure of exposure information according to the embodiment;

FIG. 6 is a flowchart showing an example of the operation to be performed when the medical information management apparatus according to the embodiment performs exposure information generation processing.

DETAILED DESCRIPTION

Figure 2:
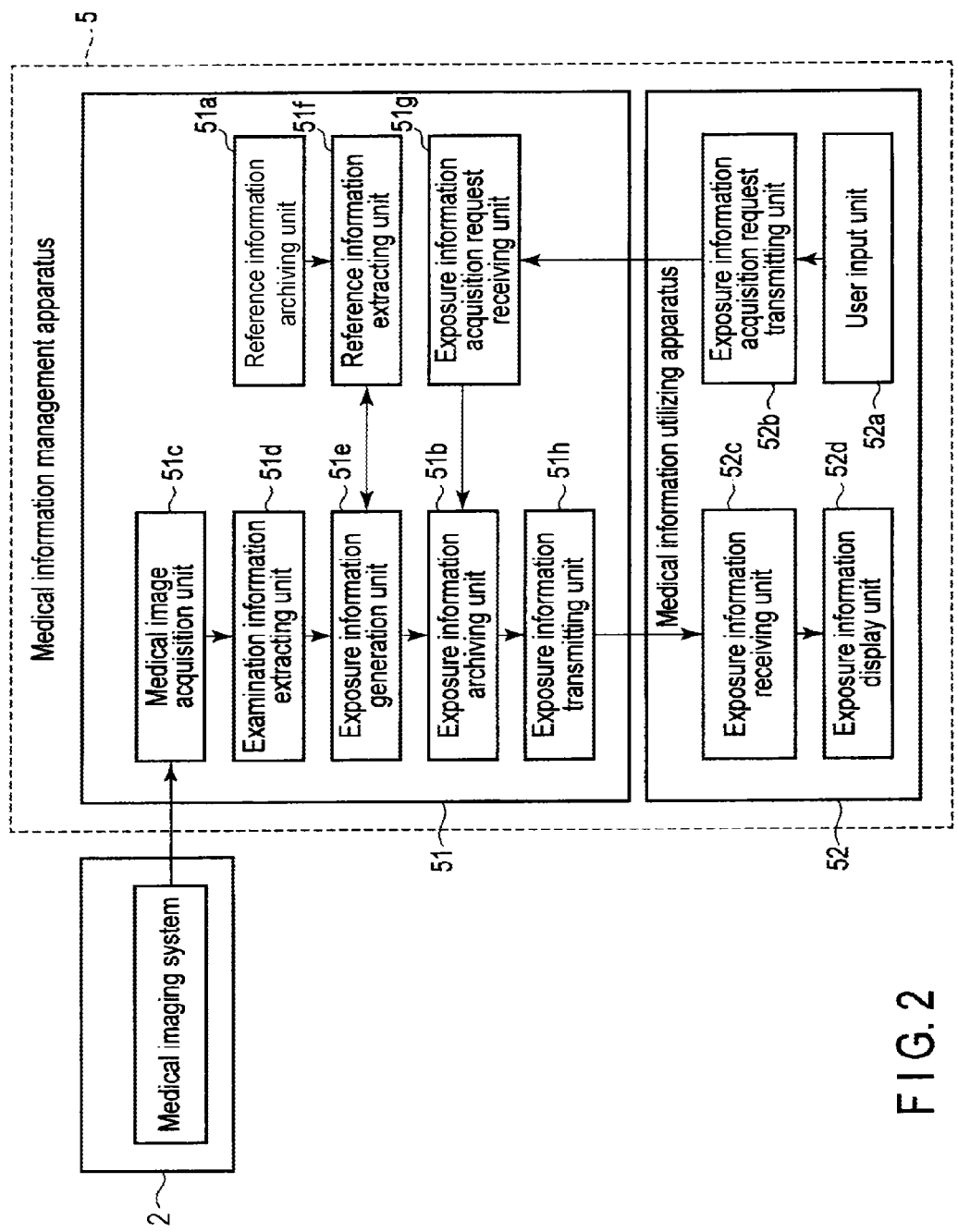
FIG. 2 is a schematic view showing an example of the schematic arrangement of the medical information management apparatus according to the embodiment.

In general, according to one embodiment, a medical information management apparatus includes an examination information acquisition unit, an archiving unit, a weight coefficient acquisition unit, and a calculation unit. The examination information acquisition unit acquires examination information including information representing an irradiation condition and an imaging region and information representing an exposure dose for each examination on the imaging region. The archiving unit archives information representing an exposure dose calculation target region classified more detailed or finer than the imaging region and a weight coefficient corresponding to the exposure dose calculation target region in association with the irradiation condition and information representing the imaging region. The weight coefficient acquisition unit acquires a weight coefficient corresponding to the exposure dose calculation target region based on the irradiation condition acquired by the examination information acquisition unit and information representing the exposure dose calculation target region archived in the archiving unit. The calculation unit calculates an exposure dose at the exposure dose calculation target region by using information representing an exposure dose for each examination and the weight coefficient.

In this embodiment, radiation to be handled is assumed to be X-ray for the sake of simplicity; however, it is actually not limited to X-ray.

FIG. 1 is a schematic view showing an example of the schematic arrangement of a medical system including medical information management information according to one embodiment. The medical system includes an examination order apparatus 1, a medical imaging system 2, a medical image apparatus 3, an interpretation report apparatus 4, and a medical information management apparatus 5. The apparatuses or systems 1 to 5 are connected to each other via a network (for example, an intra-hospital network typified by an HIS). The detailed arrangements and functions of the apparatuses or systems 1 to 5 will be described below.

The examination order apparatus 1 includes an examination order issuing apparatus 11 and an examination order management apparatus 12.

The examination order apparatus 1 executes various types of processing concerning an examination order. An examination order is information concerning an examination of obtaining a medical image by using the medical imaging system 2 and includes items such as a patient identification, patient name, examination method, and examination region. However, the items of an examination order are not limited to the above items. In addition, the examination order apparatus 1 is generally called an RIS (Radiology Information System).

The examination order issuing apparatus 11 is installed in a consulting room in which a doctor medically examines a patient. The examination order issuing apparatus 11 generates (issues) an examination order in accordance with an operation by a doctor (operator) and sends the examination order to the examination order management apparatus 12.

Upon receiving the examination order sent from the examination order issuing apparatus 11, the examination order management apparatus 12 archives the examination order and further sends the examination order to the medical imaging system 2. Note that it is possible to update archived examination orders by using the examination order issuing apparatus 11, as needed, or read out archived examination orders by using the apparatus or systems 1 to 5, as needed.

The medical imaging system 2 includes a medical imaging planning apparatus 21 and a medical imaging apparatus 22.

The medical imaging system 2 executes various types of processing concerning the imaging of a medical image in accordance with the examination order sent from the examination order apparatus 1.

Upon receiving the examination order sent from the examination order management apparatus 12, the medical imaging planning apparatus 21 causes a display device (not shown) to display the examination order. In addition, the medical imaging planning apparatus 21 generates imaging plan information in accordance with an operation by a radiological technician (operator), and sends the information to the medical imaging apparatus 22. Note that imaging plan information includes items concerning an imaging plan executed by the medical imaging apparatus 22. For example, such items include a patient identification, examination identification, patient name, scheduled imaging date, device type, imaging method and the like. However, the items concerning an imaging plan are not limited to the above items. Upon receiving the imaging plan information sent from the medical imaging planning apparatus 21, the medical imaging apparatus 22 causes a display device (not shown) to display the information. The radiological technician (operator) performs a predetermined operation while referring to the information. The medical imaging apparatus 22 captures an image of a desired region of a patient and generates medical image information of the region. In addition, the medical imaging apparatus 22 sends the generated medical image information to the medical image apparatus 3.

In addition, medical image information complies with DICOM (Digital Imaging Communications and Medicine) as a standard specification in the field of image examination. An image complying with DICOM has examination information attached to the image. Examination information includes, for example, a patient identification, examination identification, device type, imaging region, patient (object) sex, image laterality (left or right), irradiation condition, and patient exposure dose for each examination (note that the exposure dose can be replaced with the radiation dose required to generate medical image information, as needed). Note however that the items included in examination information are not limited to the above items. Note that an irradiation condition is information representing the positional relationship among an imaging region, an X-ray tube, and an X-ray detector. In this embodiment, for the sake of simplicity, an irradiation condition is described as an X-ray irradiation direction. Furthermore, this embodiment is based on the assumption that medical image information complies with DICOM. However, the present invention is not limited to this, and an existing standard specification may be used as needed.

The PACS (Picture and Archiving Communication System) 3 includes a medical image archiving apparatus 31 (examination information archiving apparatus) and a medical image observation apparatus 32 (viewer).

Upon receiving the medical image information sent from the medical imaging apparatus 22, the medical image archiving apparatus 31 archives the medical image information by writing the information in a memory or the like (not shown) in the apparatus. Note that archived medical image information can be read out by using each of the apparatuses or systems 1 to 5, as needed.

The medical image observation apparatus 32 reads out the medical image information archived in the medical image archiving apparatus 31 and causes a display device (not shown) to display the medical image information in accordance with operations by an radiologist (operator).

The interpretation report apparatus 4 includes a medical report archiving apparatus 41 and a medical report creation apparatus 42.

The interpretation report apparatus 4 executes various types of processing concerning the creation of a medical report in accordance with an operation by the radiologist (operator). A medical report compiles the observation results of medical image information obtained by the radiologist.

Upon receiving the medical report created by the medical report creation apparatus 42, the medical report archiving apparatus 41 archives the medical report by writing it in a memory or the like (not shown) in the apparatus. The archived medical report can be read out by using each of the apparatuses or systems 1 to 5, as needed.

The medical report creation apparatus 42 creates a medical report and sends it to the medical report archiving apparatus 41 in accordance with an operation by the radiologist (operator). The medical report creation apparatus 42 reads out an archived medical report and causes a display device (not shown) to display it in accordance with an operation by the radiologist.

The medical information management apparatus 5 includes a medical information archiving apparatus 51 and a medical information utilizing apparatus 52. Note that the medical information management apparatus 5 can be implemented as the medical information management apparatus 5 integrating the functions of the medical information archiving apparatus 51 and medical information utilizing apparatus 52, as shown in FIG. 2.

As shown in FIG. 2, the medical information archiving apparatus 51 includes a reference information archiving unit 51a, an exposure information archiving unit 51b, a medical image acquisition unit 51c, an examination information extracting unit 51d, an exposure information generation unit 51e, a reference information extracting unit 51f, an exposure information acquisition request receiving unit 51g, and an exposure information transmitting unit 51h. The detailed function of each of the units 51a to 51h will be described below.

As shown in FIG. 3, the reference information archiving unit 51a archives a plurality of pieces of reference information (a so-called lookup table) associating various types of items such as an imaging region included in examination information, a region irradiated with X-rays (to be written as an irradiation region or exposure dose calculation target region hereinafter), and a weight coefficient corresponding to each irradiation region. Note that while an imaging region indicates a chest region, head region, or the like, an irradiation region (exposure dose calculation target region) indicates a region as a classification more detailed or finer than an imaging region (for example, an anatomically classified region such as the lung, heart, or thyroid gland).

In addition, a combination of various types of items (a device type, imaging region, sex, image laterality, and irradiation direction in this embodiment) included in examination information in reference information is defined as a lookup sample. The above irradiation regions and weight coefficients are set in advance in correspondence with each lookup sample.

FIG. 3 shows examples of lookup samples. Lookup sample a is the one in which the chest region of a male is imaged from the front side by a CR (Computed Radiography) apparatus (written as general imaging in FIG. 3). Irradiation regions and weight coefficients are set in correspondence with this lookup sample. Since the CR apparatus is an apparatus requiring no consideration of laterality, the image laterality in lookup sample a is "N/A (not applicable)".

Lookup sample b is the one in which the chest region of a female is imaged from the front side by the CR apparatus. Irradiation regions and weight coefficients are set in correspondence with the lookup sample. Since lookup sample a differs in sex from lookup sample b, the set irradiation regions differ from each other accordingly. In other words, lookup sample b is associated with the breast as an irradiation region, whereas lookup sample a is not associated with the breast. This is because when a female is to be imaged, a careful consideration needs to be given to the exposure of mammary glands to radiation because of the possibility of breast cancer.

Lookup sample c is the one in which the chest region of a male is imaged from the back side by the CR apparatus. Irradiation regions and weight coefficients are set in correspondence with the lookup sample. Since lookup sample a differs in irradiation direction from lookup sample c, the set weight coefficients differ from each other accordingly. This is because X-rays reach the respective regions in different orders and X-ray absorptances at the respective regions differ from each other when X-ray irradiation is performed from the front side and from the back side. For example, the weight coefficient for the lung as one of the irradiation regions associated with the lookup sample a is 0.30, whereas the weight coefficient for the lung as one of the irradiation regions associated with the lookup sample c is 0.20.

Lookup sample d and lookup sample e each are the one in which the chest region of a female is imaged by a mammography. Irradiation regions and weight coefficients are set in correspondence with the lookup samples. A mammography is an apparatus designed to image a chest region only from the front direction, and hence there is no need to give any consideration to the irradiation direction. Therefore, the irradiation direction associated with each of lookup sample d and lookup sample e is "N/A (not applicable)". In addition, since a mammography is generally an apparatus designed to image each of the left and right breasts, image laterality is included in consideration. The image laterality in lookup sample d is "L (Left)", and the image laterality in lookup sample e is "R (Right)". Lookup sample f is the one in which the head region of a male is imaged by an X-ray CT apparatus. Irradiation regions and weight coefficients are set in correspondence with the lookup sample. An X-ray CT apparatus is an apparatus designed to almost uniformly irradiate a subject with X-rays from 360° directions (all directions) centered on the body axis of the object, and hence there is no need to give any consideration to image laterality and irradiation direction. Therefore, the image laterality and associated irradiation direction in lookup sample f are "N/A (not applicable)". In this embodiment, as examples of lookup samples, lookup sample a to lookup sample f are defined as shown in FIG. 3. However, lookup samples to be used are not limited to lookup sample a to lookup sample f.

Note that, as indicated by equation (1) given below, weight coefficients are set such that the total of a plurality of weight coefficients associated with a plurality of irradiation regions corresponding to one lookup sample is 1.

$$\sum_{n=0}^{n=N} W(n) = 1 \qquad (1)$$

Note that in equation (1) described above, W(n) represents a weight coefficient, N represents the number of irradiation regions set in correspondence with one lookup sample, and n represents the nth irradiation region of a plurality of irradiation regions set in correspondence with one lookup sample.

The exposure information archiving unit 51b archives exposure information (to be described later). As shown in FIG. 4, exposure information includes a patient identification, examination identification, irradiation region, and irradiation region exposure dose. Upon receiving the patient identification sent from the exposure information acquisition request receiving unit 51g, the exposure information archiving unit 51b sends exposure information including the patient identification to the exposure information transmitting unit 51h (to be described later).

The medical image acquisition unit 51c acquires medical image information archived in the medical image archiving apparatus 31 in accordance with an operation by the operator. More specifically, upon receiving a patient identification from an input interface (e.g., a mouse, keyboard, or touch panel) (not shown) operated by the operator or via a network, the medical image acquisition unit 51c acquires medical image information including the patient identification as examination information.

The examination information extracting unit 51d extracts examination information from the medical image information acquired by the medical image acquisition unit 51c. For example, in this embodiment, examination information includes a patient identification, examination identification, device type, irradiation region, sex, image laterality, irradiation direction, and exposure dose. For this reason, the examination information extracting unit 51d extracts examination information including these types of items.

The exposure information generation unit 51e selects a proper lookup sample from the reference information archiving unit 51a based on the respective types of items included in the examination information extracted by the examination information extracting unit 51d. The exposure information generation unit 51e also acquires an irradiation region and weight coefficient associated with the lookup sample selected from the reference information archiving unit 51a via the reference information extracting unit 51f. In addition, the exposure information generation unit 51e calculates and generates an irradiation region exposure dose based on the irradiation region and weight coefficient acquired via the reference information extracting unit 51f, the examination information extracted by the examination information extracting unit 51d, and equation (2) given below.

$$E(n) = S \cdot W \qquad (2)$$

Note that in equation (2) given above, E(n) represents an exposure dose for each irradiation region, S represents the exposure dose included in the examination information, W(n) represents a weight coefficient, and n represents the nth irradiation region of a plurality of irradiation regions set in correspondence with the lookup sample.

In addition, the exposure information generation unit 51e generates exposure information based on the generated irradiation region exposure dose, the acquired irradiation region, and the examination information extracted by the examination information extracting unit 51d. Moreover, the exposure information generation unit 51e writes the generated exposure information in the exposure information archiving unit 51b.

As described above, the reference information extracting unit 51f extracts an irradiation region and a weight coefficient from the reference information archiving unit 51a and sends them to the exposure information generation unit 51e in accordance with a request from the exposure information generation unit 51e.

Upon receiving the exposure information acquisition request transmitted from an exposure information acquisition request transmitting unit 52b, the exposure information acquisition request receiving unit 51g sends the patient identification included in the exposure information acquisition request to the exposure information archiving unit 51b.

Upon receiving the exposure information sent from the exposure information archiving unit 51b, the exposure information transmitting unit 51h transmits the information to an exposure information receiving unit 52c (to be described later).

The medical information utilizing apparatus 52 includes a user input unit 52a, the exposure information acquisition request transmitting unit 52b, the exposure information receiving unit 52c, and an exposure information display unit 52d, as shown in FIG. 2.

Upon receiving a patient identification from an input interface (e.g., a mouse, keyboard, or touch panel) (not shown) operated by the operator or via a network, the user input unit 52a sends the patient identification to the exposure information acquisition request transmitting unit 52b.

Upon receiving the patient identification sent from the user input unit 52a, the exposure information acquisition request transmitting unit 52b transmits an exposure information acquisition request concerning the identified patient to the exposure information acquisition request receiving unit 51g, together with the patient identification.

Upon receiving the exposure information transmitted from the exposure information transmitting unit 51h, the exposure information receiving unit 52c transmits the exposure information to the exposure information display unit 52d (to be described later).

Figure 5:
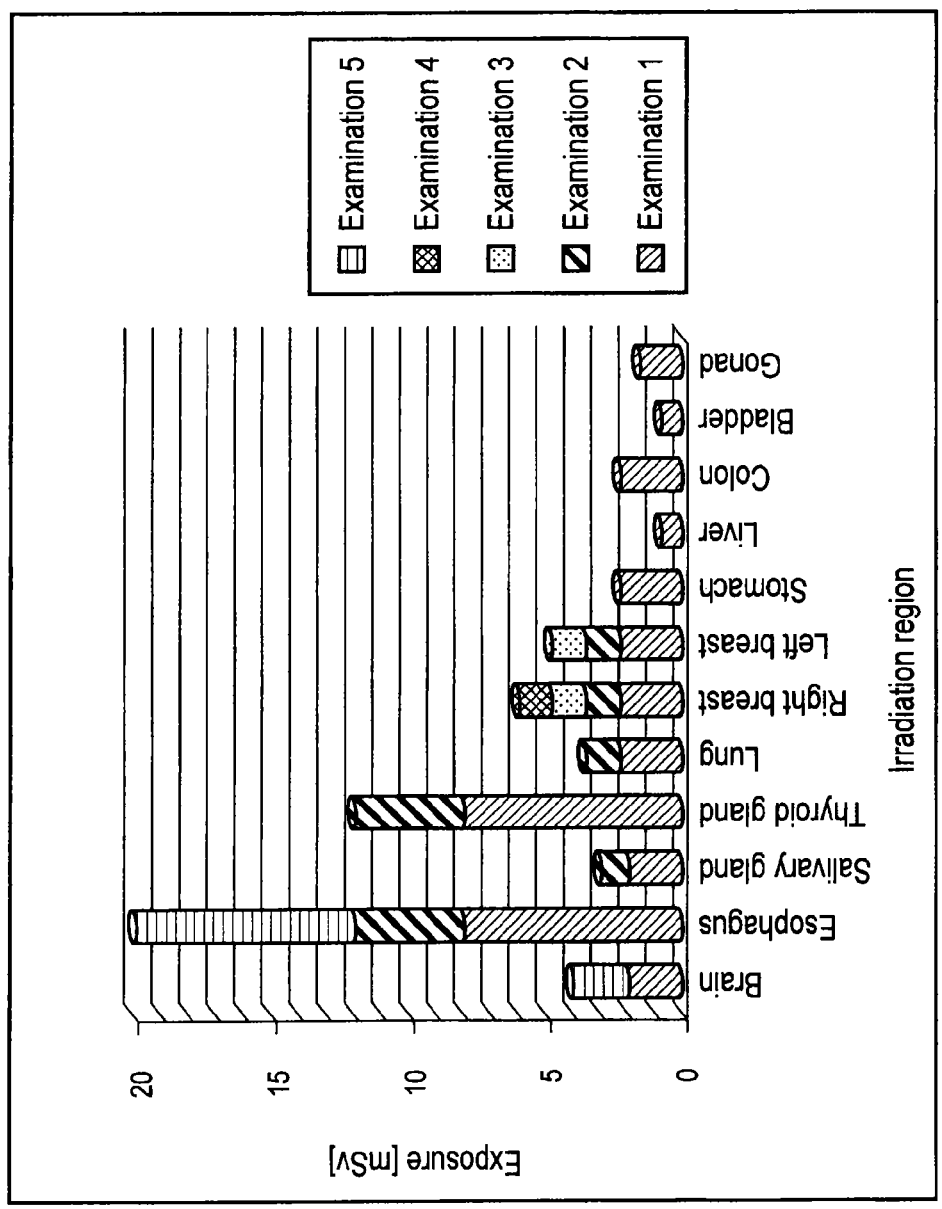
FIG. 5 is a schematic view showing an example of a screen on a display device when displaying exposure information according to the embodiment.

Upon receiving the exposure information sent from the exposure information receiving unit 52c, the exposure information display unit 52d causes a display device (not shown) to display the exposure information as shown in, for example, FIG. 5. In the example shown in FIG. 5, the ordinate of the graph represents exposure dose [mSv], and the abscissa of the graph represents irradiation region (organ or tissue) of the patient. Note that a display device (not shown) may display all past exposure information of the patient or may display only exposure information of the patient for a desired period (e.g., one year). In addition, the abscissa may indicate the transition of the exposure dose of a predetermined irradiation region by showing dates instead of irradiation regions. Furthermore, since an exposure dose equal to or more than a predetermined value may have an adverse effect on a subject (patient), a critical value may be displayed for each irradiation region.

Note that the medical information archiving apparatus 51 and the medical information utilizing apparatus 52 described above each include a CPU (Central Processing Unit) (not shown), and each CPU controls each unit.

An example of the operation to be performed when the medical information management apparatus 5 having the above arrangement performs exposure information generation processing will be described with reference to the schematic views of FIGS. 3 and 4 and the flowchart of FIG. 6. Note that various types of processing described below are executed by causing a CPU (not shown) to control the respective units in accordance with stored programs. Note however that in the following description, for the sake of descriptive convenience, "information item B indicating A" will be written as "B" A"".

First of all, the medical image acquisition unit 51c acquires medical image information archived in the medical image archiving apparatus 31 in accordance with an operation by the operator (step S1). Assume that in this case, the medical image acquisition unit 51c has received patient identification "A" from an input interface (not shown) and has acquired medical image information having the patient identification included in examination information from the medical image archiving apparatus 31 in accordance with an operation by the operator.

Subsequently, the examination information extracting unit 51d extracts the examination information included in the medical image information acquired by the medical image acquisition unit 51c (step S2). Assume that in this case, the examination information extracting unit 51d has extracted the examination information including patient identification "A", examination identification "1", device type "general imaging", imaging region "chest region", sex "male", image laterality "N/A", irradiation direction "front", and exposure dose "100".

The exposure information generation unit 51e then selects a proper lookup sample from the reference information archiving unit 51a based on the various types of items included in the examination information extracted by the examination information extracting unit 51d (step S3). Assume that in this case, the exposure information generation unit 51e has selected "lookup sample a" as a lookup sample based on device type "general imaging", imaging region "chest region", sex "male", image laterality "N/A", and irradiation direction "front" included in the extracted examination information.

Subsequently, the exposure information generation unit 51e acquires an irradiation region and weight coefficient associated with the lookup sample selected from the reference information archiving unit 51a via the reference information extracting unit 51f (step S4). Assume that in this case, the exposure information generation unit 51e has acquired irradiation regions "lung", "heart", and "thyroid gland", associated with "lookup sample a", and weight coefficients "0.20", "0.21", and "0.10" respectively corresponding to these irradiation regions.

The exposure information generation unit 51e then calculates and generates an irradiation region exposure dose based on the acquired irradiation region and weight coefficient and the examination information extracted by the examination information extracting unit 51d (step S5). In this case, the exposure information generation unit 51e calculates and generates an exposure dose for each irradiation region based on equation (2) described above. More specifically, the exposure information generation unit 51e calculates exposure dose "20 (=100×0.20)" of the lung based on acquired irradiation region "lung", weight coefficient "0.20", and exposure dose "100" included in the examination information, and generates an irradiation region exposure dose indicating exposure dose "20". Likewise, the exposure information generation unit 51e calculates exposure dose "21 (=100×0.21)" of the heart based on acquired irradiation region "heart", weight coefficient "0.21", and exposure dose "100" included in the examination information, and generates an irradiation region exposure dose indicating exposure dose "21". In addition, the exposure information generation unit 51e calculates exposure dose "10 (=100×0.10)" of the thyroid gland based on acquired irradiation region "thyroid gland", weight coefficient "0.10", and exposure dose "100" included in the examination information, and generates an irradiation region exposure dose indicating exposure dose "10".

Subsequently, the exposure information generation unit 51e generates exposure information based on the generated irradiation region exposure doses, the acquired irradiation regions, and the examination information extracted by the examination information extracting unit 51d (step S6). In this case, the exposure information generation unit 51e generates exposure information associating patient identification "A" and examination identification "1" included in the examination information, irradiation region "lung", and irradiation region exposure dose "20" with each other. Likewise, the exposure information generation unit 51e generates exposure information associating patient identification "A" and examination identification "1" included in the examination information, irradiation region "heart", and irradiation region exposure dose "21" with each other. In addition, the exposure information generation unit 51e generates exposure information associating patient identification "A" and examination identification "1" included in the examination information, irradiation region "thyroid gland", and irradiation region exposure dose "10" with each other.

Subsequently, the exposure information generation unit 51e writes the generated exposure information in the exposure information archiving unit 51b (step S7), and terminates the operation in this operation example.

According to one embodiment described above, it is possible to manage an exposure dose for each irradiation region exposed to radiation by using the arrangement including the exposure information generation unit 51e which calculates an exposure dose for each irradiation region based on the examination information included in medical image information, the irradiation region and weight coefficient set in correspondence with a selected lookup sample, and equation (2) described above.

Note that the above embodiment has described about the management of an exposure dose for each irradiation region of a predetermined patient along with an actual examination on the patient. As a modification of this embodiment, it is also possible to manage an exposure dose for each irradiation region in an examination in a general case without specifying any patient.

Note that each of the functions of the described embodiments may be implemented by one or more processing circuits, a processing circuit includes a programmed processor, as a processor includes circuitry, and a processing circuit also includes devices such as an application specific integrated circuit (ASIC) and conventional circuit components arranged to perform the recited functions.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed is:

1. A medical information management apparatus comprising:
    an examination information acquisition unit configured to acquire examination information including an irradiation condition, information representing an imaging region, and information representing an exposure dose for each examination on the imaging region;
    an archiving unit configured to archive information representing an exposure dose calculation target region classified more detailed than the imaging region and a weight coefficient corresponding to the exposure dose calculation target region in association with the irradiation condition and information representing the imaging region;
    a weight coefficient acquisition unit configured to acquire a weight coefficient corresponding to the exposure dose calculation target region based on the irradiation condition acquired by the examination information acquisition unit and the information representing the exposure dose calculation target region archived in the archiving unit; and
    a calculation unit configured to calculate an exposure dose at the exposure dose calculation target region by using the information representing an exposure dose for each examination and the weight coefficient.

2. The apparatus of claim 1, wherein the irradiation condition includes information representing an irradiation direction.

3. The apparatus of claim 1, wherein the acquisition unit acquires the examination information corresponding to received information representing an identification of a patient.

4. The apparatus of claim 1, further comprising an exposure information management unit configured to generate exposure information associating information representing the exposure dose calculation target region with the calculated exposure dose at the exposure dose calculation target region.

5. The apparatus of claim 4, wherein the exposure information includes an accumulated value of exposure doses for the each exposure dose calculation target region.

6. The apparatus of claim 1, wherein the calculation unit calculates the exposure dose on the exposure dose calculation target region by multiplying the information representing an exposure dose for each examination on the imaging region by the weight coefficient corresponding to the exposure dose calculation target region.

7. The apparatus of claim 1, wherein the each weight coefficient associated with each imaging region is set such that the sum of all the weight coefficients becomes 1.

8. A medical information management method comprising:
    acquiring examination information including an irradiation condition, information representing an imaging region, and information representing an exposure dose for each examination on the imaging region;
    acquiring a weight coefficient corresponding to an exposure dose calculation target region based on the acquired irradiation condition and information representing the exposure dose calculation target region from an archiving unit configured to archive information representing an exposure dose calculation target region classified more detailed than the imaging region and a weight coefficient corresponding to the exposure dose calculation target region in association with the irradiation condition and information representing the imaging region; and
    calculating an exposure dose at the exposure dose calculation target region by using the information representing an exposure dose for each examination and the weight coefficient.

9. The method of claim 8, wherein the irradiation condition includes information representing an irradiation direction.

10. The method of claim 8, wherein the acquiring the examination information comprises acquiring the examination information corresponding to received information representing an identification of a patient.

11. The method of claim 8, further comprising generating exposure information associating information representing the exposure dose calculation target region with the calculated exposure dose at the exposure dose calculation target region.

12. The method of claim 11, wherein the exposure information includes an accumulated value of exposure doses.

13. The method of claim 8, wherein the calculating the exposure dose comprises calculating the exposure dose on the exposure dose calculation target region by multiplying the information representing an exposure dose for each examination on the imaging region by the weight coefficient corresponding to the exposure dose calculation target region.

14. The method of claim 8, wherein the each weight coefficient associated with each imaging region is set such that the sum of all the weight coefficients becomes 1.

15. A medical system comprising at least an examination information archiving apparatus and a medical information management apparatus, with at least the two apparatuses being communicatively connected to each other,
the examination information archiving apparatus archiving examination information including an irradiation condition, information representing an imaging region, and information representing an exposure dose for each examination on the imaging region, and
the medical information management apparatus including
an examination information acquisition unit configured to acquire the examination information,
an archiving unit configured to archive information representing an exposure dose calculation target region classified more detailed than the imaging region and a weight coefficient corresponding to the exposure dose calculation target region in association with the irradiation condition and information representing the imaging region,
a weight coefficient acquisition unit configured to acquire a weight coefficient corresponding to the exposure dose calculation target region based on the irradiation condition acquired by the examination information acquisition unit and the information representing the exposure dose calculation target region archived in the archiving unit, and
a calculation unit configured to calculate an exposure dose at the exposure dose calculation target region by using the information representing an exposure dose for each examination and the weight coefficient.

16. The system of claim 15, wherein the irradiation condition includes information representing an irradiation direction.

17. The system of claim 15, wherein the acquisition unit acquires the examination information corresponding to received information representing an identification of a patient.

18. The system of claim 15, further comprising an exposure information management unit configured to generate exposure information associating information representing the exposure dose calculation target region with the calculated exposure dose at the exposure dose calculation target region.

19. The system of claim 18, wherein the exposure information includes an accumulated value of exposure doses for the each exposure dose calculation target region.

20. The system of claim 15, wherein the calculation unit calculates the exposure dose on the exposure dose calculation target region by multiplying the information representing an exposure dose for each examination on the imaging region by the weight coefficient corresponding to the exposure dose calculation target region.

21. The system of claim 15, wherein the each weight coefficient associated with each imaging region is set such that the sum of all the weight coefficients becomes 1.

\* \* \* \* \*